United States Patent

Bollag et al.

[11] Patent Number: 4,565,863
[45] Date of Patent: Jan. 21, 1986

[54] RETINOID CARBOHYDRATES

[75] Inventors: Werner Bollag, Basel; Hans J. Mayer, Füllinsdorf; Pierre-Charles Wyss, Muttenz, all of Switzerland

[73] Assignee: Hoffmann-La Roche Inc., Nutley, N.J.

[21] Appl. No.: 677,441

[22] Filed: Dec. 3, 1984

[30] Foreign Application Priority Data

Dec. 8, 1983 [CH] Switzerland ............... 6570/83

[51] Int. Cl.$^4$ ........................................... C07H 13/02
[52] U.S. Cl. .................... 536/18.2; 536/18.7; 536/53; 536/119
[58] Field of Search ............ 536/18.2, 18.7, 53, 536/119

[56] References Cited

U.S. PATENT DOCUMENTS 3,219,657 11/1965 Gaertner .......................... 536/119
4,215,215 7/1980 Bollag ............................. 542/427
4,316,983 2/1982 Bollag ............................. 536/4
4,388,312 6/1983 Terao et al. ...................... 536/53

Primary Examiner—Johnnie R. Brown
Attorney, Agent, or Firm—Jon S. Saxe; George M. Gould; William H. Epstein

[57] ABSTRACT

The novel retinoids of the formula

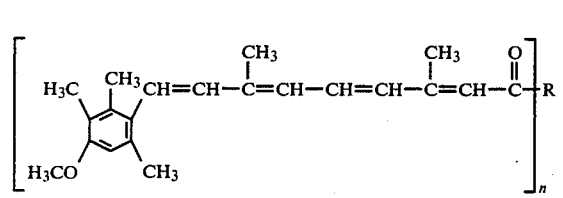

wherein R represents a residue of a sugar attached esterwise or a residue of an amino-sugar attached amidewise or of derivatives of such sugars and n is 1 or 2, can be used as medicaments, e.g. for the treatment of neoplasms, acne and psoriasis. These compounds are obtained by reacting a sugar or an aminosugar or a derivative thereof with a reactive derivative of 9-(4-methoxy-2,3,6-trimethylphenyl)-3,7-dimethyl-2,4,6,8-nonatetraenoic acid, optionally followed by the modification of reactive groups present in the reaction product.

23 Claims, No Drawings

RETINOID CARBOHYDRATES

SUMMARY OF INVENTION

In accordance with this invention retinoids of the formula

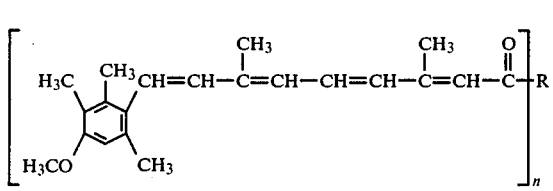

wherein R is a residue of a sugar attached ester-wise or a residue of an amino-sugar attached amide-wise or of derivatives of such sugars and n is 1 or 2, can be used as medicaments, e.g. for the treatment of neoplasms an antitumor agents, as well as for the treatment of acne and psoriasis.

DETAILED DESCRIPTION

In accordance with a preferred embodiment of this invention, R in the compound of formula I is

—$XR_1$ wherein X is —O—, —NH— or —NH(CH$_2$)$_m$O—; m is an integer of from 2 to 6; and $R_1$ is a residue obtained by removal of a hydroxy group from a member selected from the group consisting of a sugar, an aminosugar, deoxyaminosugar, deoxysugar, glycosides thereof, derivatives thereof wherein one or more of the hydroxy or amino groups contained therein are acylated derivatives thereof wherein at least two of the free hydroxy groups are acetalized and derivatives thereof.

In accordance with this invention, $R_1$ can be derived from any sugar or amino sugar residue or derivatives thereof. The sugars or amino sugar preferably are pentose or hexose monosaccharides such as glucose, fructose, mannose, galactose, ribose, xylose, glucosamine, fructosamine, mannosamine and galactosamine; as well as the disaccharides formed from pentoses or hexoses such as lactose, maltose or trehalose. The amino sugars are sugars as defined above where one or more of the free hydroxy groups have been replaced by an amino group.

The derivatives of the sugars or the amino groups are those sugars where one or more hydroxy groups have been removed from the sugar structure, i.e., the deoxysugars or the deoxyamino sugars. Other derivatives of sugars or amino sugars, or the deoxy derivatives thereof are the glycosides of the aforementioned. Among the preferred glycosides are the alkylglycosides, most preferably the lower alkyl glycosides such as methylglucoside, ethylglucoside, etc. and aminoalkylglycosides, such as aminoethyl glucoside, amino methyl glucoside, [aminoethyl]-2-deoxy-2-aminoglucoside and [aminoethyl]-N-acetyl-tri-O-acetyl-2-deoxy-2-aminoglucoside. Other derivatives of sugars, amino sugars, deoxyamino sugars, deoxysugars and glycosides thereof, are those derivatives where at least one of the amino or hydroxy groups are acylated with an appropriate acyl group such as lower alkanoyl. Another derivative of the above which are included within the retinoids of this invention are those derivatives where one or more of the hydroxy groups are acetalized with an appropriate ketone such as acetone, methyl ethyl ketone, etc. Another derivative of this invention are those derivatives where the free —CH$_2$OH group in the sugar, aminosugar, deoxysugar, deoxyaminosugar, glycosides thereof or derivatives thereof is oxidized to an —COOH group.

The double bonds in the polyene chain, i.e. the 9-(4-methoxy-2,3,6-trimethylphenyl)-3,7-dimethyl-2,4,6,8-nonatetraenyl residue in the compounds of formula I, can have the cis or trans configuration. Compounds of formula I in which the polyene chain has the all-trans configuration are preferred.

The compounds of formula I can be manufactured in accordance with the invention by reacting a sugar or an aminosugar or a derivative of such a sugar, which contains at least one free hydroxy or amino group, with a reactive derivative of 9-(4-methoxy-2,3,6-trimethylphenyl)-3,7-dimethyl-2,4,6,8-nonatetraenoic acid and, if desired, functionally modifying reactive groups present in the reaction product.

Examples of reactive derivatives of 9-(4-methoxy-2,3,6-trimethylphenyl)-3,7-dimethyl-2,4,6,8-nonatetraenoic acid are the halides, especially the chloride, reactive amides such as the imidazolide and mixed anhydrides. The acylation in accordance with the invention can be carried out in an inert organic solvent, e.g., a hydrocarbon such as benzene or toluene or an ether such as dioxan or tetrahydrofuran, in the presence of a base, e.g. an amine such as pyridine (which can simultaneously serve as the solvent). The reaction temperature is not critical. The reaction is conveniently carried out at temperatures between 0° C. and 50° C., especially at 0° C. to 30° C.

If desired, reactive groups present in the reaction product can be functionally modified. For example, O-acyl groups present in the residue R in reaction products of formula I in which R is attached amide-wise can be saponified by treatment with bases such as alkali metal alcoholates.

The compounds of formula I are of value as active substances for pharmaceuticals, e.g. for the treatment of neoplasms, especially for topical administration. Furthermore, they can be used for the treatment of acne and psoriasis, and for the treatment of inflammatory and allergic dermatoses. The compounds are distinguished, in particular, by a good tolerance, e.g. the absence of skin irritations in the case of topical administration.

The tumour-inhibiting activity of the compounds was tested on mice in which papillomae of the skin had been produced by treatment with dimethylbenzanthracene and croton oil. A regression of the papillomae was observed upon administration of compounds of formula I. Furthermore, the toxicity of the compounds was determined on the basis of their vitamin A activity. The test methodology for these investigations is described in Europ. J. Cancer Vol. 10, 731–737 (1974). The test results are compiled in Table I.

TABLE I

| Compound of Example | A-hypervitaminosis active dosage mg/kg | Tumour-inhibiting activity dosage mg/kg | % regression of the papilloma diameter |
|---|---|---|---|
| 3 | 100 | 100 | −56 |
|   |   | 50 | −48 |
| 7 | 200 | 200 | −84 |
|   |   | 80 | −72 |
|   |   | 40 | −42 |
| 8 | 200 | 200 | −72 |

TABLE I-continued

| Compound of Example | A-hypervitaminosis active dosage mg/kg | Tumour-inhibiting activity dosage mg/kg | % regression of the papilloma diameter |
|---|---|---|---|
|  |  | 100 | −41 |
| 9 | 200 | 200 | −65 |

The compounds of formula I can be used as medicaments, e.g. in the form of pharmaceutical preparations. The preparations for systemic administration can be manufactured e.g. by adding a compound of formula I as the active ingredient to non-toxic, inert, solid or liquid carriers which are customary per se in such preparations. The preparations can be administered enterally or parenterally. For enteral administration there are suitable e.g. preparations in the form or tablets, capsules, dragees, syrups, suspensions, solutions and suppositories. Preparations in the form of infusion or injection solutions are suitable for parenteral administration.

The dosages in which the process products are administered can vary according to the type of use and mode of use as well as according to the requirements of the patients.

The process products can be administered in amounts of about 5 to about 200 mg daily in one or more dosages. Capsules containing about 10 mg to about 100 mg of active substance are a preferred administration form.

The preparations can contain inert as well as pharmacodynamically active additives. Tablets or granulates e.g. can contain a series of binding agents, filling materials, carrier substances or diluents. Liquid preparations can be present, for example, in the form of a sterile solution which is miscible with water. Capsules can contain, in addition to the active substance, a filling material or thickening agent. Furthermore, flavour-improving additives, as well as substances usually used as preserving, stabilizing, moisture-retaining and emulsifying agents, salts for varying the osmotic pressure, buffers and other additives can also be present.

The previously mentioned carrier substances and diluents can be organic or inorganic substances, e.g. water, gelatine, lactose, starch, magnesium stearate, talc, gum arabic, polyalkylene glycols and the like. It is a pre-requisite that all adjuvants used in the manufacture of the preparations are non-toxic.

For topical administration the process products are conveniently used in the form of salves, tinctures, creams, solutions, lotions, sprays, suspensions and the like. Salves and creams as well as solutions are preferred. These preparations intended for topical administration can be manufactured by mixing the process products as active ingredients with non-toxic, inert, solid or liquid carriers which are customary per se in such preparations and which are suitable for topical treatment.

For topical administration there are conveniently used about 0.01 to about 0.3%, preferably 0.02 to 0.1%, solutions as well as about 0.05 to about 5%, preferably about 0.1 to about 2%, salves or creams.

An antioxidant, e.g. tocopherol, N-methyl-γ-tocopheramine as well as butylated hydroxyanisole or butylated hydroxytoluene, can be admixed with the preparations if desired.

The following Examples are intended to illustrate the invention in more detail.

EXAMPLE 1

A solution of 15.6 g of methyl α-D-glucopyranoside in 150 ml of pyridine was stirred at 0° for 2 hours under argon with a solution of 9-(4-methoxy-2,3,6-trimethylphenyl)-3,7-dimethyl-2,4,6,8-nonatetraenoyl chloride (prepared from 13 g of the corresponding acid) in 200 ml of toluene. The mixture was stirred at 0° for a further 2 hours and at room temperature for a further 2 hours, and then evaporated to dryness. Chromatography on silica gel with hexane-ethyl acetate as the elution agent yielded four products. As the least polar fraction there were obtained 2.1 g of [methyl] 2,6-bis-O-[9-(4-methoxy-2,3,6-trimethylphenyl)-3,7-dimethyl-2,4,6,8-nonatetraenoyl]-α-D-glucopyranoside, melting point 144°–145° (from ethyl acetate-isopropyl ether), $[\alpha]_D^{25} = 59.0°$ (c=1 in chloroform).

As the next product there was obtained 0.6 g of [methyl] 4-O-[4-(4-methoxy-2,3,6-trimethylphenyl)-3,7-dimethyl-2,4,6,8-nonatetraenoyl]-α-D-glucopyranoside, melting point 159°–160° (from ethyl acetate-isopropyl ether), $[\alpha]_D^{25} = +147.6°$ (c=1 in chloroform).

As the third substance there were obtained 2 g of [methyl] 2-O-[9-(4-methoxy-2,3,6-trimethylphenyl)-3,7-dimethyl-2,4,6,8-nonatetraenoyl]-α-D-glucopyranoside, melting point 197° (from ethyl acetate), $[\alpha]_D^{25} = +176.7°$ (c=1 in pyridine).

As the last product there was obtained 1 g of [methyl] 6-O-[9-(4-methoxy-2,3,6-trimethylphenyl)-3,7-dimethyl-2,4,6,8-nonatetraenoyl]-α-D-glucopyranoside as a foam, $[\alpha]_D^{25} = +28.9°$ (c=1 in chloroform).

EXAMPLE 2

In analogy to Example 1, by acylating D-trehalose dihydrate with one equivalent of acid chloride there was obtained 6,6-bis-O-[9-(4-methoxy-2,3,6-trimethylphenyl)-3,7-dimethyl-2,4,6,8-nonatetraenoyl]-D-trehalose, melting point 163°–164° (from methanol), $[\alpha]_D^{25} = +58.2°$ (c=1 in chloroform) in a yield of 8%.

EXAMPLE 3

6.9 ml of triethylamine and 4.8 ml of ethyl chloroformate were added at 0° while stirring to a suspension of 16.3 g of 9-(4-methoxy-2,3,6-trimethylphenyl)-3,7-dimethyl-2,4,6,8-nonatetraenoic acid in 200 ml of dioxan. The mixture was stirred at room temperature for 2 hours and then treated with a solution of 10.8 g of D-glucosamine hydrochloride in 15 ml of water and 6.9 ml of triethylamine. After stirring for 5 hours the precipitate was collected, washed with ether and chromatographed on silica gel. Elution with methanol-dioxan yielded 12.9 g of 2-deoxy-2-[9-(4-methoxy-2,3,6-dimethylphenyl)-3,7-dimethyl-2,4,6,8-nonatetraenamido]-D-glucose, melting point 195° (from ethanol, decomposition), $[\alpha]_D^{25} = +43.1°$ (c=1 in pyridine).

EXAMPLE 4

A solution of 19.5 g of [2-aminoethyl] 2-acetamido-3,4,6-tri-O-acetyl-2-deoxy-β-D-glucopyranoside in 400 ml of pyridine was acylated as described in Example 1. The dry residue obtained after evaporation of the reaction mixture was dissolved in 3 l of chloroform, the solution was washed with water, dried over sodium sulphate and evaporated to a syrup. Chromatography on a silica gel column with chloroform and ethanol as the elution agent yielded 19.8 g of [2-[9-(4-methoxy-2,3,6-trimethylphenyl)-3,7-dimethyl-2,4,6,8-nonatetraenamido]ethyl] 2-acetamido-3,4,6-tri-O-acetyl-2-deoxy- β-D-glycopyranoside, melting point 228° (from 2-propanol), $[α]_D^{25}= -49.9°$ (c=α in chloroform).

EXAMPLE 5

A suspension of 12 g of [2-[9-(4-methoxy-2,3,6-trimethylphenyl)-3,7-dimethyl-2,4,6,8-nonatetraenamido]ethyl]2-acetamido-3,4,6-tri-O-acetyl-2-deoxy-β-D-glycopyranoside in 500 ml of methanol was treated with 40 ml of 0.5N methanolic sodium methoxide. After stirring at room temperature for 20 minutes the crystals were filtered off, washed with methanol and recrystallized from methanol. There were obtained 7.4 g of [2-[9-(4-methoxy-2,3,6-trimethylphenyl)-3,7-dimethyl-2,4,6,8-nonatetraenamido]ethyl]2-acetamido-2-deoxy-β-D-glucopyranoside, melting point 223°, $[α]_D^{25}= -25.0°$ (c=1 in dimethyl sulphoxide).

EXAMPLE 6

A solution of 1.6 g of 1-[9-(4-methoxy-2,3,6-trimethylphenyl)-3,7-dimethyl-2,4,6,8-nonatetraenyl]imidazole and 5.62 g of β-D-glucose in 180 ml of pyridine was stirred at 30° for 5 hours after the addition of a spatula tip of imidazole sodium. Thereafter, the reaction mixture was evaporated under reduced pressure, the residue was dissolved in 500 ml of n-butanol and the solution was extracted twice with 150 ml of phosphate buffer (pH 7) each time and four times with 200 ml of ice-water each time. The organic solution was then evaporated under reduced pressure and the residue was chromatographed on 90 g of silica gel. Elution with isopropanol-methylene chloride (1:1) yielded D-glucopyranosyl 9-(4-methoxy-2,3,6-trimethylphenyl)-3,7-dimethyl-2,4,6,8-nonatetraenoate as an α,β-anomer mixture.

The imidazolide used as the starting material was prepared as follows:

25.1 g of 9-(4-methoxy-2,3,6-trimethylphenyl)-3,7-dimethyl-2,4,6,8-nonatetraenoic acid and 37.3 g of N,N-carbonyldiimidazole were dissolved in 890 ml of tetrahydrofuran and stirred at room temperature for 18 hours. The reaction mixture was then poured into 9 l of water while stirring, stirred for 15 minutes and filtered. The residue was dissolved in 1 l of methylene chloride, dried over sodium sulphate and evaporated. Recrystallization from methylene chloride-pentane yielded 1-[9-(4-methoxy-2,3,6-trimethylphenyl)-3,7-dimethyl-2,4,6,8-nonatetraenoyl]imidazole in the form of orange-yellow crystals of melting point 184°-185°.

EXAMPLE 7

7.0 g of 1-[9-(4-methoxy-2,3,6-trimethylphenyl)-3,7-dimethyl-2,4,6,8-nonatetraenoyl]imidazole and 6.34 g of D(+)-maltose were dissolved in 500 ml of pyridine and stirred at room temperature for 18 hours after the addition of a spatula tip of imidazole sodium. The reaction mixture was evaporated under reduced pressure, the residue was dissolved in 2 l of n-butanol and extracted four times with 250 ml of phosphate buffer (pH 7) each time. The organic phase was evaporated and the residue was chromatographed on 180 g of silica gel. Elution with isopropanolmethylene chloride yielded [4-O-α-D-glucopyranosyl-D-glucopyranosyl] 9-(4-methoxy-2,3,6-trimethylphenyl)-3,7-dimethyl-2,4,6,8-nonatetraenoate as an α,β-anomer mixture.

EXAMPLE 8

In analogy to Example 7, from 1-[9-(4-methoxy-2,3,6-trimethylphenyl)-3,7-dimethyl-b 2,4,6,8-nonatetraenoyl]imidazole and D-ribose there was obtained D-ribofuranosyl 9-(4-methoxy-2,3,6-trimethylphenyl)-3,7-dimethyl-2,4,6,8-nonatetraenoate as a mixture of the α- and β-anomers.

EXAMPLE 9

In analogy to Example 7, from [9-(4-methoxy-2,3,6-trimethylphenyl)-3,7-dimethyl-2,4,6,8-nonatetraenoyl]imidazole and L-rhamnose there was obtained 1-O-[9-(4-methoxy-2,3,6-trimethylphenyl)-3,7-dimethyl-2,4,6,8-nonatetraenoyl]-L-rhamnose, $[α]_D^{25}= +6.9°$ (c=1 in chloroform).

EXAMPLE 10

In analogy to Example 7, from 2-acetamido-2-deoxy-D-glucose and 1-[9-(4-methoxy-2,3,6-trimethylphenyl)-3,7-dimethyl-2,4,6,8-nonatetraenoyl]imidazole there was obtained 2-acetamido-2-deoxy-1,6-bis-O-[9-(4-methoxy-2,3,6-trimethylphenyl)-3,7-dimethyl-2,4,6,8-nonatraenoyl]-D-glucose, melting point 128°-130° C. (from ethyl acetate-hexane).

EXAMPLE 11

In analogy to Example 7, from 4,6-O-ethylidene-D-glucose and 1-[9-(4-methoxy-2,3,6-trimethylphenyl)-3,7-dimethyl-2,4,6,8-nonatetraenoyl]imidazole there was obtained 4,6-O-ethylidene-1-O-[9-(4-methoxy-2,3,6-trimethylphenyl)-3,7-dimethyl-2,4,6,8-nonatetraenoyl]-D-glucose, melting point 146°-147° C. (from tetrahydrofuran-hexane).

EXAMPLE A

Capsules for oral administration can have the following composition:

|  | Per capsule |
| --- | --- |
| Compound of formula I | 0.1 mg |
| Wax mixture | 50.5 mg |
| Vegetable oil | 98.9 mg |
| Trisodium salt of ethylenediaminetetraacetic acid | 0.5 mg |

EXAMPLE B

A salve can be manufactured in the usual manner from the following ingredients:

| | |
| --- | --- |
| Compound of formula I | 0.1 g |
| Vaseline white | 35.0 g |
| Wax white | 10.0 g |
| Paraffin oil viscous | 18.0 g |
| DEHYMULS E* | 7.0 g |
| Benzoic acid pure | 0.2 g |
| Water deionized | ad 100.0 g |

*high-molecular weight aliphatic mixed ester; supplier: Henkel

We claim:
1. A retinoid of the formula:

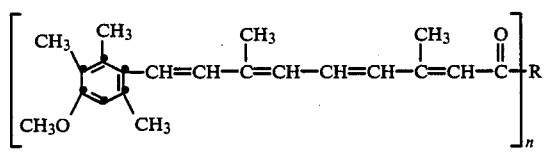

wherein n is 1 or 2; R is XR$_1$; X is —O—, —NH— or —NH(CH$_2$)$_m$—O—; m is an integer of from 2 to 6; and R$_1$ is a residue obtained by removal of a hydroxy group from a member selected from the group consisting of a sugar, an aminosugar, a deoxyaminosugar, deoxysugar, loweralkyl glycosides thereof, derivatives thereof wherein one or more of the hydroxy or amino groups contained therein are acylated with a lower alkanoyl, derivatives thereof wherein at least two of the hydroxy groups contained therein are acetalized and derivatives thereof where the free —CH$_2$OH group is oxidized to a —COOH group; with said sugars being mono- or di-saccharides of pentoses or hexoses.

2. The retinoid of claim 1 wherein R$_1$ is a sugar.

3. The retinoid of claim 2 wherein said sugar is a pentose or hexose.

4. The retinoid of claim 3 wherein said retinoid is D-glucopyranosyl-9-(4-methoxy-2,3,6-trimethyl-phenyl)-3,7-dimethyl-2,4,6,8-nonatetraenoate.

5. The retinoid of claim 3 wherein said retinoid is D-ribofuranosyl 9-(4-methoxy-2,3,6-trimethylphenyl)-3,7-dimethyl-2,4,6,8-nonatetraenoate.

6. The retinoid of claim 2 wherein said sugar is a disaccharide.

7. The retinoid of claim 6 wherein said retinoid is 6,6-bis-O-[9-(4-methoxy-2,3,6,-trimethylphenyl)-3,7-dimethyl-2,4,6,8-nonatetraenoyl]-D-trehalose.

8. The retinoid of claim 6 wherein said retinoid is [4-O-α-D-Glucopyranosyl-D-glucopyranoxyl] 9-(4-methoxy-2,3,6-trimethylphenyl)-3,7-dimethyl-2,4,6,8-nonatetraenoate.

9. The retinoid of claim 1 wherein said retinoid is a lower alkyl glycoside.

10. The retinoid of claim 9 wherein said retinoid is [methyl] 2,6-bis-O-[9-(4-methoxy-2,3,6-trimethyl-phenyl)-3,7-dimethyl-2,4,6,8-nonatetraenoyl]-α-D-glucopyranoside.

11. The retinoid of claim 9 wherein said retinoid is [methyl] 4O-[9-(4-methoxy-2,3,6-trimethylphenyl)-3,7-dimethyl-2,4,6,8-nonatetraenoyl]-α-D-glucopyranoside.

12. The retinoid of claim 9 wherein said retinoid is [methyl] 2-O-[9-(4-methoxy-2,3,6-trimethylphenyl)-3,7-dimethyl-2,4,6,8-nonatetraenoyl]-α-D-glucopyranoside.

13. The retinoid of claim 9 wherein said retinoid is [methyl] 6-O-[9-(4-methoxy-2,3,6-trimethylphenyl)-3,7-dimethyl-2,4,6,8-nonatetraenoyl]-α-D-glucopyranoside.

14. The retinoid of claim 1 wherein R$_1$ is an amino sugar.

15. The retinoid of claim 14 wherein said retinoid is 2-deoxy-2-[9-(4-methoxy-2,3,6-dimethylphenyl)-3,7-dimethyl-2,4,6,8-nonatetraenamido]-D-glucose.

16. The retinoid of claim 1 wherein R$_1$ is an amino sugar wherein one or more hydroxy or amino groups are acylated.

17. The retinoid of claim 16 wherein said retinoid is [2-[9-(4-methoxy-2,3,6-trimethylphenyl)-3,7-dimethyl-2,4,6,8-nonatetraenamido]ethyl]2-acetamido-3,4,6-tri-O-acetyl-2-deoxy-β-D-glucopyranoside.

18. The retinoid of claim 16 wherein said retinoid is [2-[9-(4-methoxy-2,3,6-trimethylphenyl)-3,7-dimethyl-2,4,6,8-nonatetraenamido]ethyl] 2-acetamido-2-deoxy-β-D-glucopyranoside.

19. The retinoid of claim 16 wherein said retinoid is 2-acetamido-2-deoxy-1,6-bis-O-[9(4-methoxy-2,3,6-trimethylphenyl)-3,7-dimethyl-2,4,6,8-nonatetraenoyl]-D-glucose.

20. The retinoid of claim 1 wherein R$_1$ is a deoxy sugar.

21. The retinoid of claim 20 wherein said retinoid is 1-O-[9-(4-methoxy-2,3,6-trimethylphenyl)-3,7-dimethyl-2,4,6,8-nonatetraenoyl]-L-rhamnose.

22. The retinoid of claim 1 wherein R$_1$ is a derivative of a sugar where at least two of the free hydroxy groups are acetalized.

23. The retinoid of claim 22 wherein said retinoid is 4,6,-ethylidene-1-O-[9-(4-methoxy-2,3,6-trimethylphenyl)-3,7-dimethyl-2,4,6,8-nonatetraenoyl]-D-glucose.

* * * * *